(12) United States Patent
Ratcliff

(10) Patent No.: US 6,277,363 B1
(45) Date of Patent: Aug. 21, 2001

(54) METHOD AND COMPOSITION FOR TREATING CHLAMYDIA INFECTION

(75) Inventor: Perry A. Ratcliff, Scottsdale, AZ (US)

(73) Assignee: Vortech, Inc., Las Vegas, NV (US)

( * ) Notice: Subject to any disclaimer, the term of this patent is extended or adjusted under 35 U.S.C. 154(b) by 0 days.

(21) Appl. No.: 09/706,212

(22) Filed: Nov. 3, 2000

Related U.S. Application Data

(60) Division of application No. 09/418,962, filed on Oct. 14, 1999, now Pat. No. 6,200,557, and a continuation-in-part of application No. 09/189,782, filed on Sep. 21, 1998, now Pat. No. 6,017,554.

(51) Int. Cl.$^7$ ...................................................... A61K 9/00
(52) U.S. Cl. .................................... 424/78.02; 424/78.07; 424/433; 424/DIG. 15; 424/601; 514/967; 514/944; 514/937; 514/931
(58) Field of Search ............................ 424/78.02, 78.07, 424/433, DIG. 15, 601; 514/967, 944, 937, 931

(56) References Cited

PUBLICATIONS

"Induction of prostaglandin release from macrophages by bacterial endotoxin", Offenbacher S. and Salvi GE, Clin Infect Dis 28(3):505–513, (1999).

"Reaction of chlorine dioxide with amino acids and peptides: Kinetics and mutagenicity studies", H. Tan, W. Wheeler and C. Wei, Mutation Research, 188:259–266 (1987).

"The Relationship Between Oral Malodor, Gingivitis and Periodontitis", P. Ratcliff and P. Johnson, Journal of Periodontology, pp. 1–14, (1999).

"Potential pathogenic mechanisms of periodontitis associated pregnancy complications", Offenbacher S., Jared HL, O'Reilly PG, Wells SR, Salvi GE, Lawrence HP, Socransky SS and Beck JD, Ann Periodontol 3(1):223–250, (1999).

"Role of periodontitis in systemic health: spontaneous preterm birth", Offenbacher S., Beck JD, Lieff S. and Slade G., J Dent Edu 62(10): 852–858, (1998).

"Oral health and systemic disease: periodontitis and cardiovascular disease", Beck JD and Offenbacher S., J Den Educ 62(10): 859–870, (1998).

"Letter to the Editor", Dr. Perry Ratcliff, J Periodontol, pp. 749–750, (Aug. 1995).

"The Inhibitiry Effect of Alcide, and Antimicrobial Drug, on Protein Synthesis in *Escherichia coli*", J. Scatina, M. Abdel--Rahman and E. Goldman Journal of Applied Toxicology, 5(6):388–394 (1985).

*Primary Examiner*—Raj Bawa
(74) *Attorney, Agent, or Firm*—Cahill, Sutton & Thomas P.L.C.

(57) ABSTRACT

A solution or gel composition containing activated chlorine dioxide and a phosphate compound, such as disodium hydrogen phosphate, sodium dihydrogen phosphate, trisodium phosphate, and sodium monofluorophosphate, is disclosed for treating a Chlamydia infection. The preferred concentration ranges are between about 0.005% to about 2.0% chlorine dioxide, and between about 0.02% to about 3.0% phosphate compound. The phosphate compound retards escape of chlorine dioxide in the pH range of 6.0 to 7.4, at which pH the chlorine dioxide becomes activated and releases sufficient chlorine dioxide to reduce motility and become lethal to the involved micro-organisms.

1 Claim, 8 Drawing Sheets

Figure 1 The efficacy of the test compound in an aqueous vehicle (Retardex™) against the lower challenge of virus.

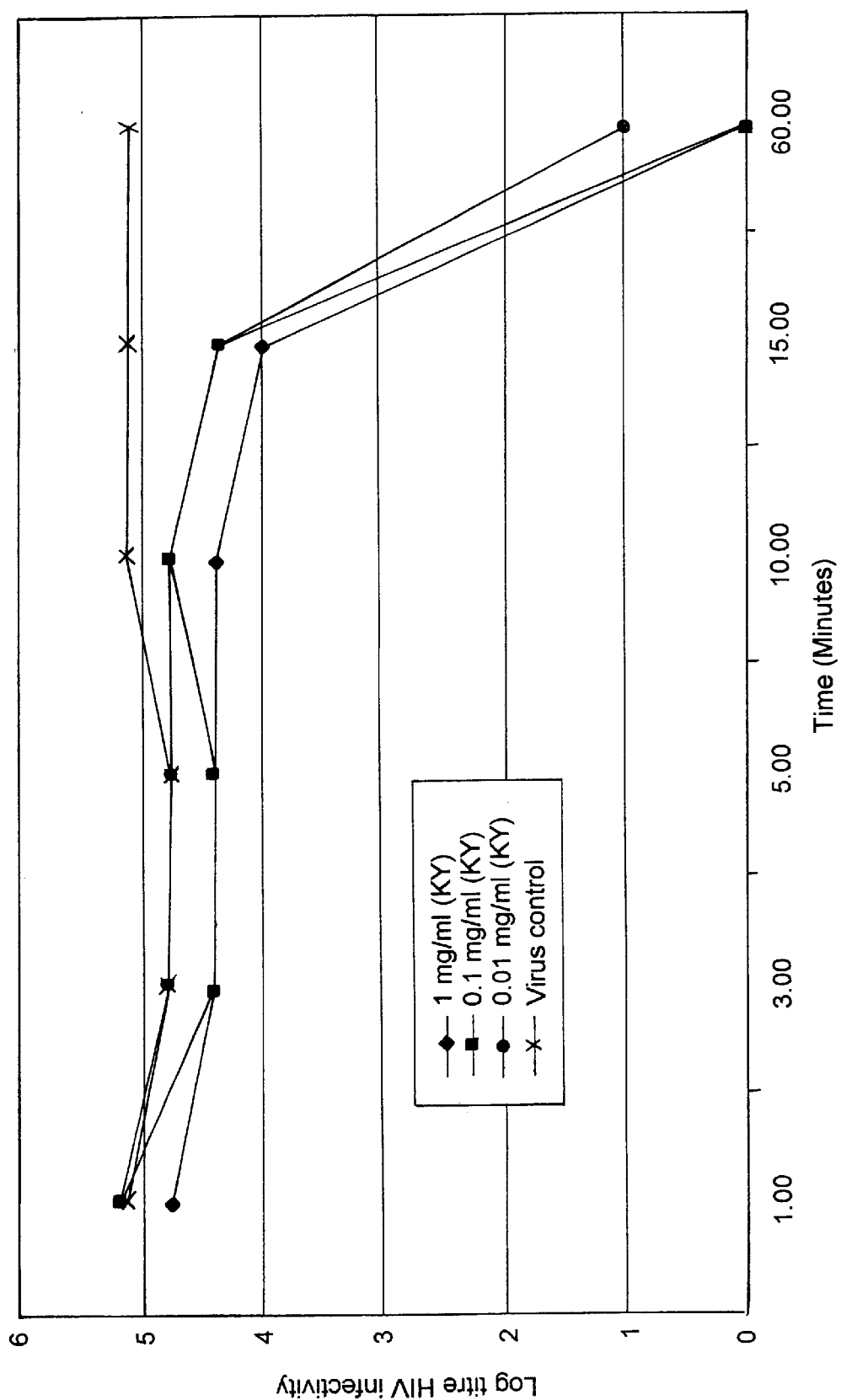
Figure 2 The efficacy of the test compound in KY jelly™ vehicle against the lower challenge of virus.

Figure 3 The efficacy of the control compound against the lower challenge of virus.

Figure 4 The efficacy of the test compound in an aqueous base (Retardex™) against the higher challenge of virus.

Figure 5 The efficacy of the test compound in a jelly base™ against the higher challenge of virus.

Figure 6  The efficacy of the control compound against the higher challenge of virus.

Figure 8 Efficacy of the test compound against the lower challenge titre of HIV-1

METHOD AND COMPOSITION FOR TREATING CHLAMYDIA INFECTION

CROSS REFERENCES TO RELATED APPLICATIONS

This application is a divisional application of an application filed Oct. 14, 1999. assigned Ser. No. 09/418,962, now U.S. Pat. No. 6,200,557, which application includes material disclosed in and claims priority to each of the provisional applications filed Oct. 15, 1998. assigned Ser. No. 60/104, 395 and provisional application filed Oct. 16, 1998, assigned Ser. No. 60/104,521 and which application is a continuation-in-part application of a patent application Ser. No. 09/189, 782, filed Sep. 21, 1998, now U.S. Pat. No. 6,017,554.

BACKGROUND OF THE INVENTION

1. Field of the Invention

The present invention is directed to a method and composition for destroying Human Immuno Virus (HIV) and other bacterial and fungus viral forms and the present invention is directed to a related method and composition which provide lubricity, stops vaginal itching and destroys HIV. More particularly, the present invention relates to the use of activated stabilized chlorine dioxide in conjunction with a phosphate compound to destroy HIV and other viral forms and wherein the phosphate compound provides stability and serves as a surfactant or nonsudsing detergent to reduce surface tension on mucosal tissues assisting in the exposure of the epithelial covering to the activated chlorine dioxide.

2. Description of Related Art

Thiols, particularly the volatile sulfur compounds such as hydrogen sulfide, methylmercaptan and dimethylsulfide, are recognized in the current literature as being major contributors to the penetration of bacterial toxins through the epithelial barrier into the underlying basal lamina and connective tissue. A. Rizzo, Periodontics, 5:233–236 (1967); W. Ng and J. Tonzetich, J. Dental Research, 63(7):994–997 (1984); M. C. Solis-Gaffar, T. J. Fischer and A. Gaffar, J. Soc. Cosmetic Chem., 30:241–247 (1979); I. Kleinberg and G. Westbay, J. Periodontal, 63(9): 768–774 (1992). The penetration of this barrier makes possible the invasion of antigenic substances such as viral and bacterial toxins and bacteria into the underlying substrate. Thus, by removing the volatile sulfur compounds and maintaining the epithelial barrier there is a reduction in the penetration capacity of antigens and microbiota (A Rizzo, Periodontics, 5:233–236 (1967); W. Ng and J. Tonzetich, J. Dental Research, 63(7): 994–997 (1984); M. C. Solis-Gaffar, T. J. Fischer and A Gaffar, J. Soc. Cosmetic Chem., 30:241–247 (1979)) as well as the destruction of the motility and the death of bacterial and viral forms.

Studies done in the mouth have demonstrated that the penetration of bacteria takes place in the presence of the volatile sulfur compounds, resulting in initiation of the inflammatory reaction including initiation of the complement cascade. I. Kleinberg and G. Westbay, J. Periodontal, 63(9): 768–774 (1992). Initiation of the inflammatory reaction and development of the complement cascade leads to an eightfold increase in the cell division or mitosis of epithelial cells in the attachment apparatus of the gingiva. W. O. Engler, S. P. Ramtiord and J. J. Hiniker, J.Periodont., 36:44–56 (1965). Because the epithelia of other orifices, and particularly vaginal epithelium, are very similar to the gingival epithelium, reactions similar to those described above for the gingival epithelium occur in all other parts of the body, as demonstrated by the occurrence of vaginitis and endometriosis of the vagina. Examples of such bacteria which may appear in any bodily orifice include *Porphyromonas* (formerly known as Bacteroides) *gingivitis Actinobacillus actinomycetemcomitans,* and Pseudomonades.

The volatile sulfur compounds are generated primarily from the polypeptide chains of the epithelial cell walls, and from the cell walls, pili, fimbrae, and flagella of microorganisms, including fungi, that are part of the normal flora of the organs of the exposed surfaces of the body. The polypeptide chains are composed of a series of amino acids including cysteine, cystine, and methionine, each of which contain sulfur side chains. The death of the microorganisms or the epithelial cells results in degradation of the polypeptide chains into their amino acid components, particularly cysteine and methionine, which then become the source of the sulfur compounds hydrogen sulfide, methylmercaptan and di-methylsulfide which alter the epithelial barrier, permitting penetration of the barrier by antigenic substances.

Penetration of the epithelial barrier by volatile sulfur compounds reduces the capacity of the tissues to protect against bacteria, virus,. fungus, and yeast forms. Tonzetich has shown, using $S^{35}$-labeled methylmercaptan, the penetration of thiol through the epitheliumr plus the basal lamina, into the underlying connective tissues where it begins degradation of collagen fibers. W. Ng and J. Tonzetich, J. Dental Research, 63(7): 994–997 (1984). In addition, it is the nature of many of the bodily orifices that they are inhabited by both pathogenic and non-pathogenic organisms. If an antibiotic is used to reduce the organisms normally present, opportunistic yeast forms and other pathogenic organisms resistant to the administered antibiotic often invade or multiply at or in the bodily orifices.

Candida species, particularly *Candida albicans,* are the yeasts that primarily affect the mouth and the female vagina. In the mouth, infection by Candida is called Thrush; in the vagina it is called vaginitis.

With the increase of patients having immunocompromising diseases such as AIDS, leukemia, diabetes and immunosuppressing diseases such as stress, alcoholism, etc., a progressively higher percentage of the human population is susceptible to invasion and growth of bacterial and fungal Candida organisms. In addition, such patients are susceptible to the development of conditions of leukoplakia such as oral hairy leukoplakia and leukoplakia vulvae.

In patients afflicted with diabetes, as well as familial history diabetes, the neutrophil, which is the first line defense cell against foreign antigens, has an altered 110 Dalton surface protein which reduces the capacity of the neutrophil to phagocytic bacteria by approximately 50%. R. J. Genco, T. E. Van Dyke, M. J. Levine, R. D. Nelson and M. E. Wilson, J. Dental Research, 65(12):1379–1391 (1986). As a result of the development of antibiotics, insulin, and more sophisticated methods of treating diabetes, early deaths of diabetics from infections have been prevented, resulting in a several-fold increase in the number of familial history diabetes in the population. Thus, the increased presence of the diabetes gene in the gene pool of the human race is rapidly increasing, resulting in a higher number of humans with an immunocompromised capacity. This fact in part explains why some women develop vaginitis whenever they are treated with antibiotic drugs.

Body orifices and adnexa are subject to the invasion of bacteria at a high level because of their exposure to the outside environment as well as due to the internal environment of the human body. As a result, there is a defense mechanism that is developed by the host to try to contain these organisms so that they do not kill the host by excessive growth. Unfortunately, some organisms gain an upper hand in this relationship and produce disease.

Chlorine dioxide is unstable in aqueous solutions at lower pH levels. It is produced commercially and shipped in an aqueous solution in its hydrolytic byproduct forms at 8.3 to 9.0 pH At that range there is complete retention of the chlorine dioxide hydrolyzed forms within the solution so that a shelf life of from 1–5 years may be achieved. When the pH of chlorine dioxide is lowered to 7.2 or below, chlorine dioxide begins to become activated and, in the gaseous form, it is available for reactivity with thiols, microorganisms, and organic debris in solution.

At present, there is an inadequate capacity of existing pharmaceutical drugs to control Candida infections (IADR symposium, March 1993). The severe diseases may be resistant to the commonly used drugs ketonideozole and nystatin, etc. Other synthetic drugs which are used systemically may have limited effects, and infections are resistant to treatment. Combinations of these drugs systemically and by suppositories may not always work.

In an in vitro study by the present inventor of Candida culture using the protocol of a simulated oral environment as stipulated by the Food and Drug Administration in the *Federal Register*, Vol. 47, No. 101 (May 25, 1982), wherein calf serum is added to the tryptic soy broth inoculated with the Candida, one ml. of the Candida culture was withdrawn and plate counted by standard techniques to determine the baseline content of the Candida population. Both a-solution and a slurry of 1 ml. paste containing 0.1% chlorine dioxide with 0.2% phosphate stabilizer plus 2 ml. of distilled water was added to the TSB broth with calf serum. Additional samples were taken at 10, 30 and 60 seconds and again plated to count the remaining Candida. It was found that at 10 seconds there was a 99+% reduction of *Candida albicans* using standard plate count techniques.

In a six month clinical trial by the present inventor, samples were taken from the gingival crevice of the mouth. After treatment of humans with a composition comprising 0.10% chlorine dioxide and 0.2% phosphate stabilizer, the inventor showed by means of standard plate count methods that during the period from baseline to six months, there was a statistically significant reduction of *Candida albicans*. This clinical trial demonstrates the capacity of a composition comprising 0.1% activated stabilized chlorine dioxide together with metallic phosphate (the latter compound acting both to stabilize the chlorine dioxide solution and also as a surfactant to break the surface tension and allow chlorine dioxide to effectively interact with the *Candida albicans* infection) to prevent and treat the development of a Candida infection.

Further details of the preparation and use of chlorine dioxide/phosphate compositions can be found in U.S. Pat. No. 5,200,171, issued Apr. 6, 1993 to Ratcliff, which is hereby incorporated by reference.

SUMMARY OF THE INVENTION

Briefly, and in accord with one embodiment of the present invention, a composition containing stabilized chlorine dioxide and a phosphate compound is disclosed as being useful in obtaining a high level kill of Human Immuno Virus (HIV) by the use of an aqueous solution or a gel containing chlorine dioxide and phosphate compound. A variant of the composition serves as a lubricant and stops vaginal itching. Stabilized chlorine dioxide is an effective agent for removing thiol compounds for deodorizing the mouth as well as deodorizing other bodily orifices, such as the vagina. The addition of activating inhibitor phosphates to the stabilized chlorine dioxide reduces surface tension and retards the rapid escape of chlorine dioxide gas at the pH range of 6.5 to 7.0 typical of orifices of the body. Preferred concentrations of stabilized chlorine dioxide compounds are in the range of between about 0.005% to about 2.0% but a range of between about 0.1% to about 2.0% may be satisfactory. The concentration of the phosphate compound, preferably disodium hydrogen phosphate, sodium dihydrogen phosphate, trisodium phosphate, and sodium monofluorophospbate, is in the range of between about 0.02 to 3.0%. A composition formed with a gel formulation or an aqueous solution capable of retaining chlorine dioxide and a phosphate will have a shelf life stability of at least one year, as demonstrated by a composition being in an oven at 40 degrees centigrade for one month. Such a composition can be used vaginally or intraorally to keep the effectiveness of the composition as a viricide or bactericide in situ for a long term basis of up to 48 hours or possibly longer (Frascella).

It is therefore a primary object of the present invention to provide a chlorine dioxide composition for destroying virus forms.

Another object of the present invention is to provide a chlorine dioxide composition for destroying HIV.

Yet another object of the present invention is to provide a topical composition for destroying viral organisms.

Still another object of the present invention is to provide a topical composition for destroying HIV.

A further object of the present invention is to provide a composition serving as a lubricant to stop vaginal itching.

A yet further object of the present invention is to provide a composition serving as a lubricant to destroy HIV.

A still further object of the present invention is to provide a method for destroying HIV.

A still further object of the present invention is to provide a method for stopping vaginal itching.

These and other objects of the present invention will become apparent to those skilled in the art as the description thereof proceeds.

BRIEF DESCRIPTION OF THE DRAWINGS

FIG. 1 illustrates the efficacy of the composition against the lower challenge of virus.

FIG. 2 illustrates the efficacy of the test composition in KY jelly against the lower challenge of virus.

FIG. 3 illustrates the efficacy of a control compound against the lower challenge of virus.

FIG. 4 illustrates the efficacy of the composition against the higher challenge of virus.

FIG. 5 illustrates the efficacy of the composition in a KY jelly base against the higher challenge of virus.

FIG. 6 illustrates the efficacy of a control compound against the higher challenge of virus.

FIG. 8 illustrates the efficacy of the test compound against the lower challenge titre of HIV-1.

DETAILED DESCRIPTION OF THE PREFERRED EMBODIMENT

Figure 7:
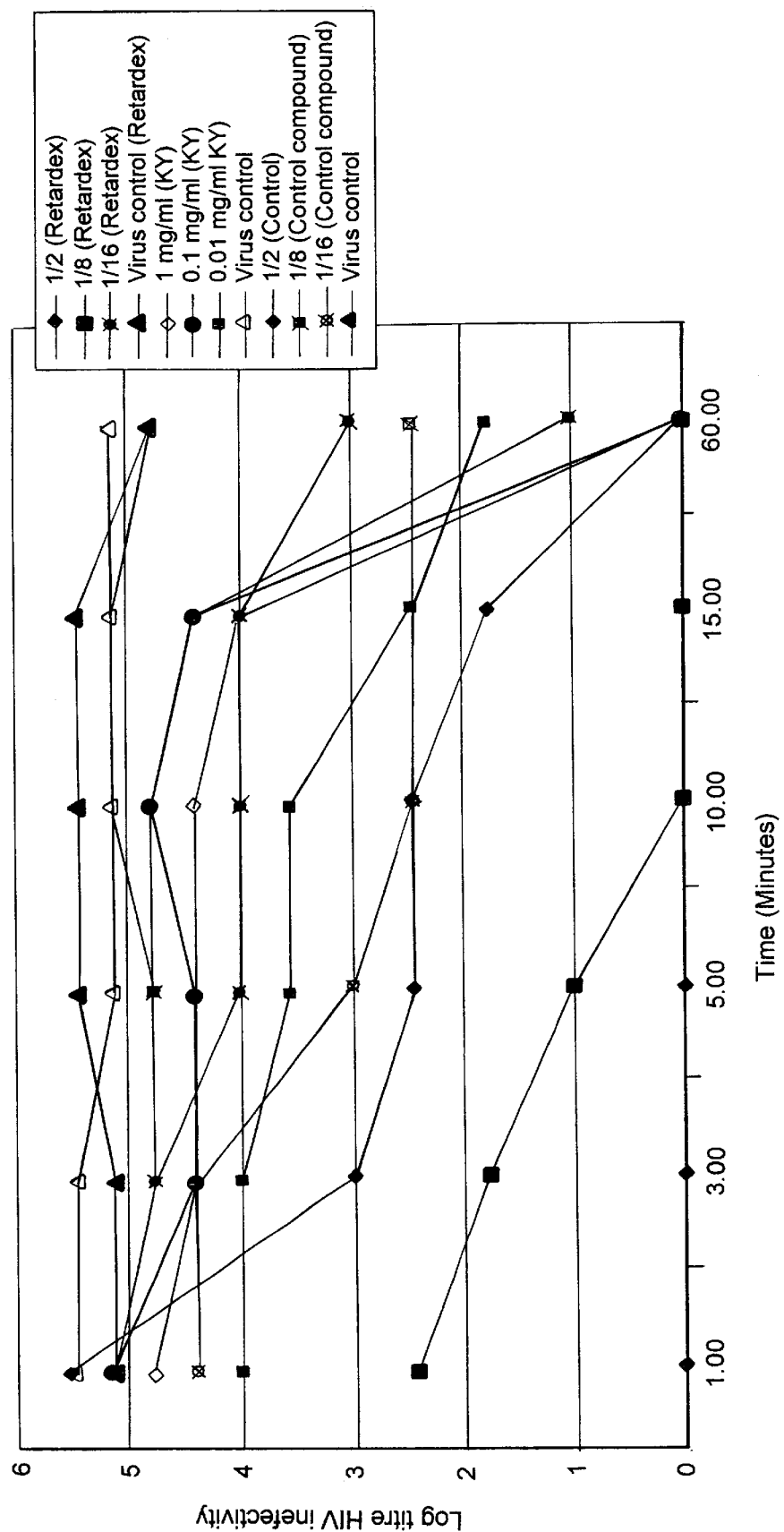
FIG. 7 illustrates log titre HIV infectivity per time.

Broadly, the present invention contemplates the use of an metallic inhibitor to stabilize $ClO_2$ in an aqueous solution and surface tension reducing agent, specifically, a phosphate compound, preferably, disodium hydrogen phosphate, sodium dihydrogen phosphate, trisodium phosphate, or sodium monofluorophosphate (in particular, trisodium phosphate, or sodium monofluorophosphate), combined with a stabilized chlorine dioxide solution, to make possible the lowering of the pH of the mixture to an optimal value of less than about 7.2 at the time the mixture is used to prevent and treat abnormal conditions of the epithelium of bodily orifices, such as those caused by fingal and bacterial infections of the rectal, vaginal, urethral, oral, nasal, ocular, and auditory canal orifices, and other abnormal conditions of the epithelium, including leukoplakia.

The present invention can be used to control the above-described bodily orifice maladies in humans, and animals which are human companions, such as dogs, cats, horses, etc., by reducing the presence of fungal and bacterial infections and leukoplakia in bodily orifices of the human and animal population, to prevent transference and cross infection from person to person or animal to person or animal to animal. Thus, the present invention can be used in both human and veterinary applications.

Clinical observations and in vitro and in vivo studies by the inventor have led to the discovery that an metallic inhibitor phosphate such as disodium monohydrogen phosphate, sodium dihydrogen phosphate, or, preferably, trisodium phosphate, or sodium monofluorophosphate, causes a reduction in surface tension, as well as stabilizing chlorine dioxide, so that the chlorine dioxide remains effective at a lower pH than was previously thought possible. In addition, the phosphate is a detergent which is used in place of other detergents for lowering surface tension and allowing the activated chlorine dioxide to become available to the convoluted surfaces of the body orifices. Effective concentration ranges are between about 0.005% to about 2.0% chlorine dioxide, and between about 0.02%–3.0% phosphate. For most patients, the preferred concentration of chlorine dioxide will be in the range of between about 0.005 to about 0.5%; in the case of extremely immunocompromised patients having runaway bacterial, fungal or viral infections, it is preferred to increase the concentration of chlorine dioxide from about 1.0 to about 2.0%.

The permeability of mucus epithelial tissue is increased substantially by exposure to thiol compounds including hydrogen sulfide ($H_2S$) and methylmercaptan ($CH_3$—SH) and dimethylsulfide ($CH_3$—S—$CH_3$). In a Candida infection, there is increased inflammation and degeneration of epithelial cells, which break down into thiols, including the above sulfur compounds. A vicious cycle is established, leading to an environment for the increase of Candida growth. If the patient is immunocompromised with AIDS, the problem is exacerbated with ulcerations that could increase the probability of sexually transmitted disease. Likewise, a non-AIDS patient such as with apathous ulcers could be more exposed to sexually transmitted disease.

The following examples further illustrate various features of the invention but are intended in no way to limit the scope of the invention which is defined in the appended claims.

EXAMPLE 1

The stability of Chlorine Dioxide at Ph 6.8 in the Presence of Phosphate

Materials:
1. Purogene (2% $ClO_2$), Lot #8907.41, 1 gallon, Manufactured by BIO-Cide, International, P.O. Box 2700, Norman, Okla. 73070.
2. Sodium Phosphate, monobasic, dibasic, and tribasic.

Methods:

A 10% solution of monobasic sodium phosphate was prepared in distilled water. Ten ml was placed into each of four beakers. One of each of the four beakers received 1, 2.5, 5, and 10 ml of chlorine dioxide concentrate (2% $ClO_2$), respectively. All solutions were diluted to 90 ml with distilled water, adjusted to pH 6.8 with 1N NaOH and 1N HCl, diluted to 100 ml and placed in screw cap bottles.

Solutions containing dibasic and tribasic sodium phosphate and a distilled water blank control were prepared in a similar manner.

Chlorine dioxide content and pH was determined for each solution on days 0, 7, 14, 21 and 28 in accordance with Standard Methods for the Examination of Water and Wastewater, 17th edition, 1989.

Results and Summary:

As shown in Table 1, the content of chlorine dioxide was stable in all sodium phosphate solutions and distilled water control over the 28 day test period. The pH of all samples ranged from 6.1 to 7.6.

TABLE 1

RESULTS SHOWING THE STABILITY OF CHLORINE DIOXIDE SOLUTION AT pH 6.8 IN DISTILLED WATER 1% SODIUM PHOSPHATE, MONOBASIC, DIBASIC, AND TRIBASIC

| | Theoretical | DAY | | | | | | | | | |
|---|---|---|---|---|---|---|---|---|---|---|---|
| | | 0 | | 7 | | 14 | | 21 | | 28 | |
| SOLUTION | % $ClO_2$ | pH | % $ClO_2$ | pH | % $ClO_2$ | pH | % $ClO_2$ | pH | % $ClO_2$ | pH | % $ClO_2$ |
| Distilled Water | 0.02 | 6.8 | 0.02 | 6.9 | 0.02 | 6.9 | 0.02 | 6.5 | 0.02 | 6.5 | 0.02 |
| | 0.05 | 6.8 | 0.05 | 6.9 | 0.05 | 6.9 | 0.05 | 7.1 | 0.05 | 6.9 | 0.05 |
| | 0.1 | 6.8 | 0.1 | 6.9 | 0.1 | 7.0 | 0.1 | 7.7 | 0.1 | 7.6 | 0.1 |
| | 0.2 | 6.8 | 0.2 | 6.9 | 0.2 | 6.9 | 0.2 | 7.2 | 0.2 | 7.2 | 0.2 |
| 0/0 $Na_2 HPO_{11}$ | 0.02 | 6.8 | 0.02 | 6.1 | 0.02 | 6.7 | 0.02 | 6.7 | 0.02 | 6.8 | 0.02 |
| (Disodium | 0.05 | 6.8 | 0.05 | 6.8 | 0.05 | 6.8 | 0.05 | 6.8 | 0.05 | 6.8 | 0.05 |
| hydrogen | 0.1 | 6.8 | 0.1 | 6.9 | 0.1 | 6.9 | 0.1 | 6.8 | 0.1 | 6.8 | 0.1 |
| phosphate) | 0.2 | 6.8 | 0.2 | 6.9 | 0.2 | 6.9 | 0.2 | 6.9 | 0.2 | 6.8 | 0.2 |
| 0/0 $Na_3PO_4$ | 0.02 | 6.8 | 0.02 | 6.7 | 0.02 | 6.8 | 0.02 | 6.7 | 0.02 | 6.8 | 0.02 |
| (Trisodium | 0.05 | 6.8 | 0.05 | 6.8 | 0.05 | 6.8 | 0.05 | 6.8 | 0.05 | 6.9 | 0.05 |
| phosphate) | 0.1 | 6.8 | 0.1 | 6.8 | 0.1 | 6.8 | 0.1 | 6.9 | 0.1 | 6.9 | 0.1 |
| | 0.2 | 6.8 | 0.2 | 6.8 | 0.2 | 6.8 | 0.2 | 6.9 | 0.2 | 6.9 | 0.2 |

TABLE 1-continued

RESULTS SHOWING THE STABILITY OF CHLORINE DIOXIDE SOLUTION
AT pH 6.8 IN DISTILLED WATER 1% SODIUM PHOSPHATE,
MONOBASIC, DIBASIC, AND TRIBASIC

| | | DAY | | | | | | | | | |
|---|---|---|---|---|---|---|---|---|---|---|---|
| | Theoretical | 0 | | 7 | | 14 | | 21 | | 28 | |
| SOLUTION | % $ClO_2$ | pH | % $ClO_2$ | pH | % $ClO_2$ | pH | % $ClO_2$ | pH | % $ClO_2$ | pH | % $ClO_2$ |
| 0/0 $Na_3PO_4$ | 0.02 | 6.8 | 0.02 | 6.8 | 0.02 | 6.4 | 0.02 | 6.9 | 0.02 | 7.0 | 0.02 |
| (Trisodium | 0.05 | 6.8 | 0.05 | 7.0 | 0.05 | 7.1 | 0.05 | 6.9 | 0.05 | 7.0 | 0.05 |
| phosphate) | 0.1 | 6.8 | 0.1 | 7.5 | 0.1 | 7.5 | 0.1 | 7.0 | 0.1 | 6.9 | 0.1 |
| | 0.2 | 6.8 | 0.2 | 7.0 | 0.2 | 7.1 | 0.2 | 6.9 | 0.2 | 6.9 | 0.2 |

EXAMPLE 2

The stability of Chlorine Dioxide at Ph 6.8 in the Presence of 0.2% Phosphate

The following is an example of how to test the stability of chlorine dioxide at pH 6.8 in the presence of 0.2% phosphate.

Materials:

1. Purogene (2% $ClO_2$), Lot #8907.41, 1 gallon, Manufactured by BIO-Cide, International, P.O. Box 2700, Norman, Okla. 73070.
2. Sodium Phosphate, monobasic, dibasic, and tribasic.

Methods:

A 0.2% solution of monobasic sodium phosphate is prepared in distilled water. Ten ml is placed into each of four beakers. One of each of the four beakers receives 1, 2.5, 5, and 10 ml of chlorine dioxide concentrate (2% $ClO_2$), respectively. All solutions were diluted to 90 ml with distilled water, adjusted to pH 6.8 with 1N NaOH and 1N HCl, diluted to 100 ml and placed in screw cap bottles.

Solutions containing dibasic and tribasic sodium phosphate and a distilled water blank control are prepared in a similar manner.

Chlorine dioxide content and pH is determined for each solution on days 0, 7, 14, 21 and 28 in accordance with Standard Methods for the Examination of Water and Wastewater, 17th edition, 1989, in order to determine the stability of chlorine dioxide over time.

EXAMPLE 3

The Effectiveness of Chlorine Dioxide in Phosphate Mixture Against Candida albicans Materials:

1. Purogene (2% chlorine dioxide), lot #8907:41, manufactured by BIO-CIDE International, Inc., P.O. Box 2700, Norman, Okla. 73070.
2. Test Organism: Candida albicans (ATCC#18804)
3. Saline, 0.9% NaCl.
4. Butterfield's Buffer phosphate dilutent (BFB), pH 7.2.
5. Sterile 15% sodium thiosulfate.
6. Blood agar.
7. Stop watch.
8. Sterile 1N HCl and 1N NaOH.
9. pH meter.
10. McFarland nephelometer tube No. 1. Density of this tube is equivalent to a bacterial suspension of $3 \times 10^8$ organisms per ml.
11. N,N-diethyl-p-phenylenediamine (DPD reagent).
12. Phosphate buffer reagent.
13. Sodium dihydrogen phosphate, $NaH_2PO_4.7H_2O$.
14. Trisodium phosphate, $Na_3PO_4.12H_2O$.
15. Sodium monofluorophosphate, $Na_2FPO_3$, Ref No. OB 12837, manufactured by Albright and Wilson, P.O. Box 80, Oldbury, Narley, West Midlands, B694LN, England.

DPD reagent and phosphate buffer reagent were prepared in accord, with Standard Methods for the Examination of Water and Wastewater, 17th Edition, p. 9–54 (1989).

Methods:

1. Test Solutions:

A ten percent sodium dihydrogen phosphate solution was prepared in distilled water. Ten ml was placed into each of five beakers. One of each of the five beakers received 0, 1, 2.5, 5, and 10 ml of chlorine dioxide concentrate (2% $ClO_2$), respectively. All solutions were diluted to 90 ml with distilled water, adjusted to pH 6.0 with 1N NaOH and 1N HCl, diluted to 100 ml and placed in screw cap bottles. Solutions containing 0 ppm chlorine dioxide were filter sterilized prior to use.

Solutions containing trisodium phosphate and sodium monofluorophosphate were prepared in a similar manner.

II. Test Suspensions:

Suspensions of the Candida albicans organism were prepared in Butterfield's buffer from 48 hour agar cultures and turbidity adjusted to a McFarland Tube #1. Subsequently 0.1 ml of this suspension was diluted in 50 ml of saline. The diluted microorganism suspensions were now ready for use.

III. Test Procedure:

1. Test:

One ml of test suspension was aliquoted into each of five sterile 16×125 mm screw cap tubes. Each of the five tubes received 4 ml of a solution containing either 0, 200, 500, 1000, or 2000 ppm chlorine dioxide in 1% sodium dihydrogen phosphate. Each tube was shaken for ten seconds and immediately inactivated with 0.25 ml 15% sodium thiosulfate. Solutions containing 1% trisodium phosphate and 1% sodium monofluorophosphate were handled in a similar manner.

2. Controls:

One ml of test suspension was dispensed into two sterile 16×125 mm screw cap tubes. Each tube received 4 ml 2000 ppm chlorine dioxide in 1% sodium dihydrogen phosphate. The first tube received 0.25 ml sodium thiosulfate, while the second tube received none. Subsequently each tube was tested for residual chlorine dioxide by adding 0.3 ml phosphate buffer reagent and 0.3 ml DPD reagent to each tube.

Neutralized tubes were colorless, while nonneutralized tubes were pink. Solutions of trisodium phosphate and sodium monofluorophosphate containing 2,000 ppm chlorine dioxide were handled in a similar manner.

One ml test suspension of the *Candida albacans* organism was treated with 4 ml Butterfield's buffer and 0.25 ml 10% sodium thiosulfate as a negative control.

After inactivation with sodium thiosulfate all tubes were plate counted.

Sterility tests on all reagents were run parallel to experiments by plate counted method. The plate counted method and sterility tests were conducted in accord with Standard Methods for the Examination of Water and Wastewater, 17th Edition, p. 9–54 (1989).

Results and Summary:

As shown in Table 2, 99–100% of the *Candida albicans* organisms were killed when challenged with 1,000 ppm (0.1%) –2,000 ppm (0.2%) chlorine dioxide in either 1% sodium dihydrogen phosphate or trisodium phosphate. Chlorine dioxide concentrations of 200 (0.02%) and 500 ppm (0.05%) in the presence of phosphates demonstrated marginal bactericidal activity against *C.albicans* (39–51% kill).

TABLE 2

RESULTS SHOWING THE BACTERICIDAL ACTIVITY OF CHLORINE DIOXIDE IN PHOSPHATE SOLUTIONS AT pH 6.0 AGAINST CANDIDA ALBICANS

| $ClO_2$ (PPM) | Negative Control* | PHOSPHATE SOLUTION | |
|---|---|---|---|
| | | 1% $NaH_2HPO_4$ | 1% $Na_2PO_4$ |
| 0 | 95,000** | 64,000 (33)*** | 55,000 (42) |
| 200 | ND | 58,000 (39) | 64,000 (33) |
| 500 | ND | 47,000 (51) | 32,000 (66) |
| 1000 | ND | 250 (99) | 0 (100) |
| 2000 | ND | 17 (99) | 5 (99) |

*Butterfield's buffer
**Organisms/ml
***Percent Kill
ND - Not done

EXAMPLE 4

The Effectiveness of Chlorine Dioxide in Phosphate Mixture against *Candida albicans* in the Presence and Absence of Serum Materials:
1. Purogene, Lot #8907:41, 1 gallon (contains 2% $ClO_2$), manufactured by BIO-CIDE International, Inc., P.O. Box 2700, Norman, Okla. 73070.
2. Test Organism: *Candida albicans* (ATCC #18804) obtained from American Type Culture Collection, (ATCC) 12301 Parklawn Drive, Rockville, Md. 20852.
3. 15% Sodium thiosulfate ($Na_2S_2O_3$)
4. Plate Count agar
5. Newborn calf serum, Colostrum free, Lot #30P7485, Gibco Laboratories, Grand Island, N.Y., 14072.
6. Butterfield's Buffer, pH 7.2
7. Trisodium phosphate, $Na_3PO_4 \cdot 12H_2O$, Sigma Chemical Co., St. Louis Mo. 63178.

Methods:

Chlorine dioxide solution having concentrations of 0, 200, 500, 1,000 and 2,000 mg/L were prepared from Purogene concentrate. Each $ClO_2$ concentration was prepared to contain 0.5% tribasic sodium phosphate (i.e., trisodium phosphate, $Na_3PO_4 \cdot 12H_2O$). In a similar manner, chlorine dioxide solutions of 0, 200, 500, 1,000 and 2,000 mg/L were prepared, with each solution containing 1.0% tribasic sodium phosphate. The pH of the chlorine dioxide/phosphate mixture was adjusted to 6.5 with 1N and 6N hydrochloric acid.

Tryptic Soy Broth (100 ml) was innoculated with *Candida albicans* and incubated 24 hours at 35° C. After incubation, the cells were washed three times with Butterfield's buffer and resuspended in 100 ml buffer.

Testing in the absence of Serum:

Chlorine dioxide-phosphate solutions (100 ml) were dispensed into sterile 16×125 mm screw cap tubes, 9 ml/tube. Three tubes were prepared for each $ClO_2$ concentration. One ml of washed *C.albicans* suspension was added to one tube of each $ClO_2$ concentration, and mixed vigorously for 10 seconds. One minute after addition of $ClO_2$, 2 ml of 15% sodium thiosulfate ($Na_2S_2O_3$) was added to each tube and well mixed to inactivate $ClO_2$ in the mixture. The procedure was repeated twice with the remaining tubes except that $ClO_2$ was inactivated with sodium thiosulfate after 2 and 5 minutes respectively.

Serial ten-fold dilutions ($10^{-1}$–$10^{-5}$) of *Candida albicans*/$ClO_2$ mixtures were prepared in Butterfield's buffer. Simultaneously, one ml of each dilution was transferred to a sterile 15 mm petri dish. Then 10 ml of plate count agar at 45–47° C. was added to each plate, and the plates were swirled and allowed to solidify. Plates were inverted and incubated 76 hours at 35° C., and colonies counted.

Testing in Presence of Serum:

Chlorine dioxide-phosphate solutions, were aliquoted, 8 ml tube. Three tubes were prepared per $ClO_2$ concentration. Fifty ml washed *C.albicans* suspension was added with 50 ml newborn calf serum. 2 ml of the serum-*C.albicans* suspension was added to test tubes and processed as described above.

Results:

Results showing percent kill of *Candida albicans* as a result of application of chlorine dioxide-phosphate solutions are shown in Tables 3 and 4.

TABLE 3

Results Showing Bactericidal Activity of Chlorine Dioxide-Phosphate (0.5%) Solutions at pH 6.5 Against Candida Albicans

| TIME | $ClO_2$ w/out Serum (ppm) | | | | $ClO_2$ w/Serum (ppm) | | | |
|---|---|---|---|---|---|---|---|---|
| (Seconds) | 200 | 500 | 1000 | 2000 | 200 | 500 | 1000 | 2000 |
| 1 | 33* | 44 | 99+ | 99+ | <10 | 27 | 18 | 36 |
| 2 | 13 | 33 | 99+ | 99+ | 40 | 30 | 30 | 30 |
| 3 | 29 | 35 | 99+ | 99+ | 13 | <10 | <10 | ND |

*Percent Kill
ND - Not done
+greater than

TABLE 4

Results Showing Bactericidal Activity of Chlorine Dioxide-Phosphate (1%) Solutions at pH 6.5 Against Candida Albicans

| TIME | $ClO_2$ w/out Serum (ppm) | | | | $ClO_2$ w/Serum (ppm) | | | |
|---|---|---|---|---|---|---|---|---|
| (Seconds) | 200 | 500 | 1000 | 2000 | 200 | 500 | 1000 | 2000 |
| 1 | 30* | 65 | 99+ | 99+ | <10 | <10 | <10 | <10 |
| 2 | 37 | 47 | 99+ | 99+ | 19 | <10 | 29 | 19 |
| 3 | 17 | ND | 99+ | 99+ | <10 | <10 | <10 | <10 |

*Percent Kill
ND - Not done
+greater than

EXAMPLE 5

The Effectiveness of Chlorine Dioxide in Phosphate Mixture against Actinobacillus Actinomycetemcomitans in the Presence and Absence of Serum Materials:

1. Purogene, Lot #8907:41, 1 gallon (contains 2% $ClO_2$), manufactured by BIO-CIDE International, Inc., P.O. Box 2700, Norman, Okla. 73070.
2. Actinobacillus actinomycetemcomitans, ATCC #29522, obtained from American Type Culture Collection, 12301, Parklawn Drive, Rockville, Md. 20852.
3. 15% Sodium thiosulfate ($Na_2S_2O_3$)
4. Plate Count agar
5. Newborn calf serum, Colostrum free, Lot #30P7485, Gibco Laboratories, Grand Island, N.Y., 14072.
6. Butterfield's Buffer, pH 7.2
7. Trisodium phosphate, $Na_3PO_4.12H_2O$, Sigma Chemical Co., St. Louis Mo. 63178

Methods:

Chlorine dioxide solutions having concentrations of 1,000 and 2,000 mg/L were prepared from Purogene concentrate. Each $ClO_2$ concentration was prepared to contain 0.2% sodium phosphate, tribasic (i.e., trisodium phosphate, $Na_3PO_4.12H_2O$). The pH of the chlorine dioxide/phosphate mixture was adjusted to 6.5 with 1N hydrochloric acid.

Three chocolate agar plates were inoculated with *Actinobacillus actinomycetemcomitans* and incubated 48 hours at 35° C. in a candle jar. After incubation, cells were scraped from the plates with a cotton swab and suspended in 100 ml buffer. 50 ml of this suspension was diluted with 50 ml buffer, while the other 50 ml was diluted with 50 ml serum.

Testing in the absence of Serum:

Chlorine dioxide-phosphate solutions (100 ml) were dispensed into sterile 150 ml beakers containing magnetic stir bars. While stirring on a magnetic mixer, a 10 ml portion of *A. actinomycetemcomitans*-buffer suspension was added. At 10, 30 and 60 second intervals, 10 ml was removed from the beaker and transferred to a 16×125 mm tube which contained 2ml 15% sodium thiosulfate. The tube was capped, mixed, and a plate count was performed employing chocolate agar as the growth media, in accord with the methods described in *FDA Bacteriological Analytical Manual*, 6th edition, 1984, chapters 4, 17, herein incorporated by reference.

Testing in Presence of Serum:

Testing in the presence of serum was handled in a similar manner, except that an *Actinobacillus actinomycetemcomitans*-serum suspension was substituted for the *Actinobacillus actinomycetemcomitans*-buffer suspension.

Results:

Results showing percent kill of *Actinobacillus actinomycetemcomitans* following application of the chlorine dioxide-phosphate solutions are shown in Table 5.

TABLE 5

Results Showing Bactericidal Activity of Chlorine Dioxide-Phosphate (0.2%) Solutions at pH 6.5 Against Actinobacillus Actinomycetemcomitans

| TIME | $ClO_2$ w/out Serum (ppm) | | $ClO_2$ w/Serum (ppm) | |
| --- | --- | --- | --- | --- |
| (Seconds) | 1000 | 2000 | 1000 | 2000 |
| 10 | 99* | 99+ | 99+ | 99+ |
| 30 | 99+ | 99+ | 99+ | 99+ |
| 60 | 99+ | 99+ | 99+ | 99+ |

*Percent Kill
+greater than

EXAMPLE 6

The Effectiveness of Chlorine Dioxide in Phosphate Mixture against Porphyromonas Gingivalis in the Presence and Absence of Serum Materials:

1. Purogene, Lot #8907:41, 1 gallon (contains 2% $ClO_2$), manufactured by BIO-CIDE International, Inc., P.O. Box 2700, Norman, Okla. 73070.
2. Porphyromonas (formerly known as Bacteroides) gingivalis, ATCC #33277, obtained from American Type Culture Collection, 12301 Parklawn Drive, Rockville, Md. 20852.
3. 15% Sodium thiosulfate ($Na_2S_2O_3$)
4. Plate Count agar
5. Newborn calf serum, Colostrum free, lot #30P7485, Gibco Laboratories, Grand Island, N.Y., 14072.
6. Butterfield's Buffer, pH 7.2
7. Trisodium phosphate, $Na_3PO_4.12H_2O$, Signa Chemical Co., St. Louis Mo. 63178.

Methods:

Chlorine dioxide solutions having concentrations of 1,000 and 2,000 mg/L were prepared from Purogene concentrate. Each $ClO_2$ concentration was prepared to contain 0.2% sodium phosphate, tribasic (i.e., trisodium phosphate, $Na_3PO_4.12H_2O$). The pH of the chlorine dioxide/phosphate mixture was adjusted to 6.5 with 1N hydrochloric acid. Three anaerobic BAP plates were inoculated with *gingivitis* (ATCC 33277) and incubated 72 hours at 35° C. After incubation, cells were scraped from the plates with a cotton swab and suspended in 100 ml buffer. 50 ml of this suspension was diluted with 50 ml buffer, while the other 50ml was diluted with 50 ml serum.

Testing in the Absence of Serum:

Chlorine dioxide-phosphate solutions (100 ml) were dispensed into sterile 150 ml beakers containing magnetic stir bars. While stirring on a magnetic mixer, a 10 ml portion of *P.gingivalis*-buffer suspension was added. At 10, 30 and 60 second intervals, 10 ml was removed from the beaker and transferred to a 16×25 mm tube which contained 2 ml 15% sodium thiosulfate. Tube was capped, mixed, and an anaerobic plate count was performed using anaerobic blood agar in accord with the methods described in *FDA Bacteriological Analytical Manual*, 6th edition, 1984, chapter 17.

Testing in Presence of Serum:

Testing in the presence of serum was handled in a similar manner to that described immediately above, except that a *Porphyromonas gingivalis*-serum suspension was substituted for the *Porphyromonas gingivalis*-buffer suspension.

Results:

Results showing percent kill of *Porphyromonas gingivalis* by application of chlorine dioxide-phosphate solutions are shown in Table 6.

TABLE 6

Results Showing Bactericidal Activity of Chlorine Dioxide-Phosphate (0.2%) Solutions at pH 6.5 Against Porphyromonas Gingivalis

| TIME | $ClO_2$ w/out Serum (ppm) | | $ClO_2$ w/Serum (ppm) | |
|---|---|---|---|---|
| (Seconds) | 1000 | 2000 | 1000 | 2000 |
| 10 | 89* | 99+ | 82 | 86 |
| 30 | 99+ | 99+ | 84 | 97 |
| 60 | 99+ | 99+ | 94 | 99 |

*Percent Kill
+greater than

EXAMPLE 7

A boy diagnosed as having Thrush was treated with the drug ketonizole for two weeks. The Candida were not controlled. The boy was then treated with a mouthrinse solution and toothpaste both of which contained as the effective ingredient a composition comprising 0.1% chlorine dioxide together with 0.2% trisodium phosphate. The boy's Thrush infection was brought under control within 3 days. The treating pediatrician was surprised and did not understand how the boy's recovery could happen so quickly.

EXAMPLE 8

The present inventor has treated hairy leukoplakia present on the tongue of AIDS-infected patients. The daily use of a toothpaste and mouthrinse, both of which contained as the effective ingredient a composition comprising 0.1% chlorine dioxide together with 0.2% trisodium phosphate, resulted in the disappearance of the hairy leukoplakia within 14 days. When the chlorine dioxide/phosphate-containing products were withdrawn, the hairy leukoplakia returned within 14 days. When the same products were again administered, the hairy leukoplakia again disappeared.

EXAMPLE 9

Hypothetically, the following composition may be prepared:

Stabilized chlorine dioxide 0.1%
Phosphate compound 0.05%

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the vagina of a patient afflicted with vaginitis. It is predicted that the patient will experience a cessation of vaginitis symptoms as a result of the regular administration of the composition.

EXAMPLE 10

Hypothetically, the following composition may be prepared:

Stabilized chlorine dioxide 0.1%
Phosphate compound 0.05%

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the vagina of a patient afflicted with leukoplakia vulvae. It is predicted that the patient will experience a cessation of the leukoplakia vulvae symptoms as a result of the regular administration of the composition.

EXAMPLE 11

Hypothetically, the following composition may be prepared:

Stabilized chlorine dioxide 0.1%
Phosphate compound 0.05%

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the urethra of a patient infected in that orifice with *Actinobacillus actinomycetemcomitans*. It is predicted that the patient will experience a cessation of symptoms of the infection as a result of the regular administration of the composition.

EXAMPLE 12

Hypothetically, the following composition may be prepared:

Stabilized chlorine dioxide 0.1%
Phosphate compound 0.05%

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the vagina of a patient infected in that orifice with *Porphyromonas gingivalis*. It is predicted that the patient will experience a cessation of symptoms of the infection as a result of the regular administration of the composition.

EXAMPLE 13

Hypothetically, the following composition may be prepared:

Stabilized chlorine dioxide 0.1%
Phosphate compound 0.05%

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the rectum of a patient infected in that orifice with *Porphyromonas gingivalis*. It is predicted that the patient will experience a cessation of symptoms of the infection as a result of the regular administration of the composition.

EXAMPLE 14

Hypothetically, the following composition may be prepared:

Stabilized chlorine dioxide 0.1%
Phosphate compound 0.05%

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the auditory canal of a patient infected in that orifice with *Actinobacillus actinomycetemcomitans*. It is predicted that the patient will experience a cessation of symptoms of the infection as a result of the regular administration of the composition.

EXAMPLE 15

Hypothetically, the following composition may be prepared:

Stabilized chlorine dioxide 0.1%

Phosphate compound 0.05%

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the nasal canal of a patient infected in that orifice with *Porphyromonas gingivalis*. It is predicted that the patient will experience a cessation of symptoms of the infection as a result of the regular administration of the composition.

EXAMPLE 16

Hypothetically, the following composition may be prepared:

Stabilized chlorine dioxide 0.1%

Phosphate compound 0.05%

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the ocular canal of a patient infected in that orifice with *Actinobacillus actinomycetemcomitans*. It is predicted that the patient will experience a cessation of symptoms of the infection as a result of the regular administration of the composition.

EXAMPLE 17

Hypothetically, the following composition may be prepared:

Stabilized chlorine dioxide 0.1–2.0%

Phosphate compound 0.05%

Preferable phosphate compounds include disodium hydrogen phosphate, sodium dihydrogen phosphate, trisodium phosphate, or sodium monofluorophosphate, in particular trisodium phosphate or sodium monofluorophosphate.

The above composition may be applied on a daily basis to the bodily orifices of a severely immunocompromised patient afflicted with leukoplakia, and with opportunistic bacterial and fungal infections. It is predicted that the patient will experience a cessation of leukoplakia and symptoms of infection as a result of the regular administration of the composition.

EXAMPLE 18

A secretary in the employ of the present inventor developed a vaginitis. She called for an appointment with her gynecologist only to learn that she could not be seen for several days. Because of the extreme itching, and knowing, as a consequence of her employment with the present inventor, that activated chlorine dioxide would kill Candida, she of her own initiation and volition used as a douche a mouthrinse developed by the present inventor, which mouthrinse contains 0.1% activated chlorine dioxide and 0.2% trisodium phosphate. She reported that she was asymptomatic immediately upon application of the above composition, with no itching. She took a wet cloth and applied the above composition locally, in the vicinity of the vagina, for three or four days, with no recurrent symptoms.

Vaginal itching is a common complaint of women. The products available today take a consequential period of time to be effective. A composition having chlorine dioxide and a phosphate compound as the primary active ingredients can provide an effective lubricant that will stop and/or prevent the development of itching from the vagina or other body parts.

Vaginal itching is primarily from *Candida albicans*. Other Candida species may complicate the problem. Ratcliff and Brenneman have shown the in vitro effectiveness of chlorine dioxide ($ClO_2$) solution. A concentration of stabilized chlorine dioxide of about 0.1% in solution will kill Candida at 97.5% in 30 seconds in vitro. Clinical research acquired by the inventor has shown that a concentration of about 0.1% of chlorine dioxide in solution can stop growth of Candida species. Such termination of growth will terminate the clinical manifestations of itching. Continued use on a twice weekly basis will prevent the development of itching.

This composition is a mixture of glucono-delta lactone, glycerine and hydroxyethyl cellulose. To this mixture is added stabilized chlorine dioxide and a phosphate compound in purified deionized water to give the mixture a viscosity for easy application to the vagina or other areas of the body with an applicator. Unlike petroleum jelly, which may adhere to vaginal walls and mask the early symptoms of an infection, this composition will make a personal lubricant that provides a safe way to replenish personal moisture that feels natural. It helps to enhance sexual pleasure at the same time it provides protection against vaginal itching through Candida kill. The composition will also reduce inflammation by eliminating hydrogen sulfide and methyl mercaptan which are facilitating permeation agents for the penetration of lipopolysacchardie antigen into and through the epithelial wall of the vagina.

An ideal formulation by volume could be:

| | |
|---|---|
| Glycerin | 12.0% |
| Hydroxyethyl cellulose | 1.0% |
| Glucono delta lactone | 0.6% |
| Chlorine dioxide | 0.1% in deionized water |

In the alternative, carboxymethyl cellulose may be substituted for hydroxyethyl cellulose. It is to be noted that the preferred concentration of chlorine dioxide is about 0.1% but a concentration in the range of about 0.005% to about 2.0% will be effective. The phosphate compound mixed with the chlorine dioxide solution has a range of concentration of about 0.02% to about 3.0%.

Stabilized chlorine dioxide has been used as a vehicle for the control of microorganisms and the subsequent damage to the tissues of the host. This invention is proposed as a means whereby this deleterious adverse process is intercepted by the use of stabilized chlorine dioxide in an aqueous solution or in a gel. This can be applied to various parts of the body. For example, it can be injected as a gel into the space between the gingiva and the tooth to keep the products there from allowing the ingress of antigen due to the presence of cysteine, methionine, hydrogen sulfide and methyl mercaptan. Also, it will destroy the amino acids so important to bacterial replication.

Amino acids are the building blocks for protein. No organism can survive without protein being a part of its structural formulation. Studies have shown that the amino acids are destroyed by chlorine dioxide at varying amounts, depending on the amino acid, but particularly with cysteine, methionine and tryptophan. These prevent the formulation of the building blocks to make proteins which could be used as the cell walls for daughter cells as well as the formation of DNA, RNA, pili and fimbrae as a part of the replication process of protein for bacterial daughter cells.

Methyl mercaptan has a deleterious effect on fibroblasts and fibrocytes which stimulate the whole degenerative process including vascular changes, prostaglandin $E_2$ changes, Interleukin-1 Beta changes, and other molecular changes that participate in the process of the breakdown of soft and hard tissues.

The administration of a composition or preparation of a stabilized chlorine dioxide stabilized by a mineral salt such as a phosphate (preferably trisodium or disodium phosphate) in solution or in a gel will benefit a patient as it will prevent the triggering of a number of mechanisms which have been shown in the literature of such things as the increased numbers of pre-mature, low birthweight babies, aggravation of diabetes, etc. S. Offenbacker, H. L. Jarediel, P. G O'Reilly, S. R. Wells, G. E. Salvi, H. P. Lawrence, S. S. Socransky, Jo Beck, Ann Periodontal 3(1):233–5 (1998). The stabilized chlorine dioxide preparation is especially useful in the kill of virus forms, reflected in Tables 7 and 8 shown below. In the case of HIV, it creates an automune reaction which at this point in time there is no known means of assurance for recovery. Application of chlorine dioxide to the target area of an infection(s) would provide the opportunity to destroy the virus and could be used in body orifices to prevent the multiplication of HIV to the detriment of the host. This is equally true for other viral forms that may invade organs or tissues because other virus forms may be destroyed by chlorine dioxide attacking the outer viral glycoprotein coat. Other viral forms include but are not limited to Herpes virus, Papiloma virus, rabies, Epstein-Barr virus, influenza virus and poliomyelitis virus.

TABLE 7

PRELIMINARY RESULTS FOR TEST COMPOUND
(CHLORINE DIOXIDE IN KY JELLY BASE)

| VIRUS CHALLENGE TITRE | COMPOUND CONCENTRATION (mg) | VIRUS TITRATION AFTER TREATMENT | LOG REDUCTION IN VIRUS TITRE |
|---|---|---|---|
| $HIV_{-1}$ IIIB $10^6$ $TCID_{50}$ | 1 | $10^{2.4}$ | 4.5 |
|  | 0.1 | $10^{4.7}$ | 2.2 |
|  | 0.01 | $10^{5.4}$ | 2.5 |
|  | 0.001 | $10^{6.0}$ | 0.9 |
|  | None | $10^{6.9}$ | Not applicable |
| $HIV_{-1}$ IIIB $10^3$ $TCID_{50}$ | 1 |  | 4.7 |
|  | 0.1 |  | 4.7 |
|  | 0.01 | $10^{0.96}$ | 3.7 |
|  | 0.001 | $10^3$ | 1.7 |
|  | None | $10^{4.7}$ | Not applicable |

TABLE 8

PRELIMINARY RESULTS FOR TEST COMPOUND
(CHLORINE DIOXIDE IN TOOTHPASTE BASE)

| VIRUS CHALLENGE TITRE | COMPOUND CONCENTRATION (mg) | VIRUS TITRATION AFTER TREATMENT | LOG REDUCTION IN VIRUS TITRE |
|---|---|---|---|
| $HIV_{-1}$ IIIB $10^6$ $TCID_{50}$ | 1 | $10^{5.4}$ | 0.88 |
|  | 0.1 | $10^{6.0}$ | 0.28 |
|  | 0.01 | $10^{6.0}$ | 0.28 |
|  | 0.001 | $10^{6.0}$ | 0.28 |
|  | None | $10^{6.28}$ | Not applicable |
| $HIV_{-1}$ IIIB $10^3$ $TCID_{50}$ | 1 | $10^{4.4}$ | 0.3 |
|  | 0.1 | $10^{4.7}$ | 0.0 |
|  | 0.01 | $10^{4.4}$ | 0.3 |
|  | 0.001 | $10^{4.4}$ | 0.3 |
|  | None | $10^{4.7}$ | Not applicable |

A gel whose principal component is either carbomethyl cellulose or carboethyl cellulose together with lubricants, delta lactone, and other ingredients currently being used in vaginal gels makes an adequate vehicle for the administration of stabilized chlorine dioxide gel into vaginal cavity. This, then, will prevent the development of such diseases in Candida infections, growth of Neisseria gonorrhea and viral forms such as HIV. Incomplete studies suggest the application of the stabilized chlorine dioxide phosphate solution to a specimen of male host sperm stops the motility of the sperm within a maximum of 15 minutes. (Ratcliff)

In view of the above, it is demonstrated that the use of a gel or aqueous solution containing stabilized chlorine dioxide can act as an agent to prevent vaginal infections of *Candida albicans,* Neisseria gonorrhea and HIV.

STUDY

The purpose and objective of the study was to determine whether $ClO_2$ in two vehicles, possesses virucidal activity against HIV-$1_{IIIB}$ a composition of stabilized chlorine dioxide and a phosphate. The composition was an oral rinse sold by Rowpar Pharmaceuticals, Inc. under the registered trademark "Retardex" and contained chlorine dioxide in a concentration of about 0.1% and trisodium phosphate in a concentration of about 0.1–0.3%. The study was divided into two states: a) determination of cellular toxicity of the test compounds against C8166 cells; and b) determination of the virucidal effects of the test compound against HIV-$1_{IIIB}$. The results of this study has been divided into similar sections describing the results obtained and conclusions reached at each stage.

MATERIALS AND METHODS

Test compounds

The test compounds were supplied as 0.10% concentration Chlorine dioxide and 0.20% concentration trisodium phosphate in an aqueous vehicle (Retardex® Oral Rinse and in KY jelly™ as the vehicle.

Cell Cultures

The Human T-cell line C8166 was used for toxicity and virustatic assays. These cells were maintained in RPMI 1640 medium (Sigma Chemical Company, UK) supplemented with 10% heat-inactivated foetal calf serum (FCS), 2 mM L-glutamine, 100 ug/ml penicillin, 100 µg/ml streptomycin and 5×105 M 2-Mercaptoethanol (Sigma Chemical Company, UK) according to current Retroscreen Ltd Standard Operating Procedures (SOPs).

Virus titration

Virus titrations where performed according to Retroscreen Ltd Standard Operating Procedures (SOPs).

CELLULAR TOXICITY

Method

1. The cellular toxicity of different concentrations of the test compounds against the C8166 cells was determined after ten days.
2. C8166 cells (approx. 5×10$^5$ cells/ml) were pelleted and re-suspended in four concentrations of the test compound, i.e., 200 µg/ml, 100 µg/ml and 25 µg/ml.
3. Cells re-suspended with growth medium alone were used as negative controls.
4. The cell/drug mixtures (1 ml) were added to tissue culture flasks.
5. The viability of the cells was tested by the trypan blue exclusion method after 10 days.
6. 90 µl from each well was mixed with 10 µl of trypan blue and transferred onto a Kova slide for cell counting. ps Cellular Toxicity Results The results are shown in Tables 9 and 10 below. They are presented as percentage viable cells for each drug concentration.

TABLE 9

CELLULAR TOXICITY OF CHLORINE DIOXIDE AND PHOSPHATE COMPOSITION IN AN AQUEOUS VEHICLE

| CONCENTRATION | % VIABLE CELLS |
| --- | --- |
| CONTROL | 98% |
| 1/256 | 85 |
| 1/128 | 75 |
| 1/64 | 72 |
| 1/32 | 61 |
| 1/16 | 47 |

TABLE 10

CELLULAR TOXICITY OF CHLORINE DIOXIDE AND PHOSPHATE COMPOSITION IN A KY JELLY VEHICLE

| CONCENTRATION | % VIABLE CELLS |
| --- | --- |
| CONTROL | 78 |
| 0.001 | 81 |
| 0.01 | 78 |
| 0.1 | 78 |
| 1 | 78 |
| 10 | 78 |

Cellular toxicity of chlorine dioxide in an aqueous vehicle

In the assay system the test compound in an aqueous vehicle was found to reduce the viability of the C8166 cells by 53% at a dilution of 1/16. At a concentration 1/256 we see only a slight reduction in cell viability to the control cells.

Cellular toxicity of chlorine dioxide in a KY jelly™ vehicle

In the assay system the chlorine dioxide in a KY jelly™ vehicle did not appear to be toxic at the test concentrations used. These concentrations chosen where the highest that could easily dissolve in tissue culture media.

Determination of the virustatic effects of the test compounds is reviewed below and illustrated in FIGS. 1 to 8.

The virucidal efficacy of the test compound in both vehicles was determined following current Retroscreen Ltd SOPs.

Results

Virucidal Activity of the Test Compound in an Aqueous Vehicle

The test compound in the aqueous vehicle was effective against both the higher and lower challenge titres of the virus. Against the lower challenge titre we observed a substantial reduction in the residual virus titre to below that detectable by our assay system with the highest concentration tested (1/256). At the 1/512dilution we observed almost three logs reduction in residual virus titre (99.9%) after 1 minute contact time. After 10 minutes contact time the level of residual virus was reduced to below the limits of our detection system. Even at the lowest concentration tested we observed a reduction of almost 1 log after only 1 minute and over a two log reduction (99%) was observed after five minutes.

At the higher challenge titre of the virus we also observe a rapid reduction in residual virus at the dilution with over 1 log (90%) of virus killed within 3 minutes.

Virucidal Activity of the Test Compound in a KY jelly Vehicle

In the KY jelly vehicle the test compound was not as rapid. At one, three and five minutes contact time less than 1 log of virus is killed. However after 10 minutes against the higher challenge of virus just over one log of virus is killed, and against the lower challenge of virus just under one log was killed. After fifteen minutes contact time greater than one log of virus was killed for both the lower and higher challenge titres.

After 60 minutes contact time approximately five logs of virus has been killed in both the lower and higher challenge groups.

Conclusion

In both vehicles the test compound is effective at killing HIV-$1_{IIIB}$ as determined by the assay system.

In the aqueous vehicle the effect of the test compound is very rapid with a greater than 99.9% reduction in viral titre within one minute at the highest concentration tested against the lower challenge titre of virus.

In the KY jelly vehicle the rapidity of killing was markedly less, but still a greater than 90% reduction in viral titre was observed after 10 minutes and greater than 99.9% reduction in viral titres after 60 minutes against both challenge titres of virus.

Archive Statement

The dedicated laboratory books, study protocol and final report plus any other relevant information (e.g. Certificates of Analysis for chemicals used in the study) will be held in the secure archive at the Retroscreen Ltd premises, 64 Turner Street, Whitechapel, London, El 2AD under the supervision of the archivist. The period of storage will be not less than 2 years.

As set forth above, the earlier described lubricant will also have the capability of serving as a viricide. In particular, it will have the capability of destroying HIV.

In the practice of methods to use the compounds of the present invention, an effective amount of the chlorine dioxide/phosphate composition is administered to the subject in need of, or desiring, such treatment. These compounds or compositions may be administered by any of a variety of routes depending upon the specific end use, including topically, as a lotion, creme or solution, by lavage, suppository, or as a nasal drop or spray.

The most suitable route in any given case will depend upon the use, particular active ingredient, the subject involved, and the judgment of the medical practitioner.

A further aspect of the present invention relates to pharmaceutical compositions containing as active ingredients a compound of the present invention which compositions comprise such compound in admixture with a pharmaceutically acceptable, nontoxic carrier. As mentioned above, such compositions may be prepared for use for topical application, particularly in the form of liquid solutions, suspensions, semi-solids, salves or creams, suppositories, or intranasally particularly in the form of nasal drops or aerosols.

It will be readily apparent to those skilled in the art that a number of modifications and changes can be made without departing from the spirit and scope of the present invention. Therefore, it is not intended that the invention be limited by the illustrative examples but only by the claims which follow.

I claim:

1. A method for treating a Chlamydia infection, said method consists of the step of applying a composition consisting of a topical preparation having a pH in the range of about 6.0 to about 7.4 and selected from the group consisting of liquid solutions, suspensions, semi-solids, salves, creams, gels, and suppositories, wherein the topical preparation consists of chlorine dioxide in a concentration in the range of about 0.005% to about 2.0% by volume and a phosphate compound selected from the group consisting of disodium hydrogen phosphate, sodium dihydrogen phosphate, trisodium phosphate, and sodium monofluorophosphate in a concentration of about 0.02% to about 3.0% by volume to retard escape of chlorine dioxide from the composition and to increase the shelf life of the composition.

* * * * *